United States Patent [19]

Hoppe et al.

[11] Patent Number: 5,895,643
[45] Date of Patent: Apr. 20, 1999

[54] DEODORIZING AND ANTI-MICROBIAL COMPOSITIONS FOR USE IN COSMETIC OR TOPICAL PREPARATIONS

[75] Inventors: Udo Hoppe; Martina Liebl, both of Hamburg; Gerhard Sauermann, Wiemersdorf; Bernd Traupe; Florian Wolf, both of Hamburg, all of Germany

[73] Assignee: Beiersdorf AG, Hamburg, Germany

[21] Appl. No.: 08/722,030

[22] PCT Filed: Mar. 31, 1995

[86] PCT No.: PCT/EP95/01213

§ 371 Date: Dec. 9, 1996

§ 102(e) Date: Dec. 9, 1996

[87] PCT Pub. No.: WO95/26708

PCT Pub. Date: Oct. 12, 1995

[30] Foreign Application Priority Data

Apr. 5, 1994 [DE] Germany .................. 44 11 664

[51] Int. Cl.$^6$ ..................................... A61K 7/32

[52] U.S. Cl. ................. 424/65; 424/401; 514/739
[58] Field of Search ................. 424/65, 401; 514/739

[56] References Cited

U.S. PATENT DOCUMENTS 4,921,694  5/1990  Hoppe et al. .................. 424/65
5,690,919  11/1997  Röckl et al. .................. 424/65

*Primary Examiner*—Shelley A. Dodson
*Assistant Examiner*—Michael A. Williamson
*Attorney, Agent, or Firm*—Sprung Kramer Schaefer & Briscoe

[57] ABSTRACT

Deodorizing or antibacterial compositions, in particular for use in cosmetic or topical formulations, characterized in that they comprise a) at least one 3,7,11-trimethyl-2,6,10-dodecatrien-1-ol,
b) at least one phenyl hydroxyalkyl ether having one, two or three carbon atoms in the alkyl radical,
c) at least one glycerol monoester of a short-chain or medium-chain fatty acid and
d) optionally glycerol monolaurate.

10 Claims, No Drawings

DEODORIZING AND ANTI-MICROBIAL COMPOSITIONS FOR USE IN COSMETIC OR TOPICAL PREPARATIONS

The invention relates to deodorizing and antimicrobial compositions for use in cosmetic or topical Formulations, in particular deodorizing cosmetic compositions.

Deodorizing cosmetic compositions are employed in particular for suppressing unpleasant body odour which forms as a result of the formation of intensely smelling decomposition products due to the action of certain skin bacteria on the initially largely odourless apocrine perspiration under the influence of heat and moisture.

In addition to molecules which absorb odours, two main classes of products are currently known for combating bad odours resulting from perspiration.

On the one hand, antiperspirant agents based on products which suppress or severely inhibit the formation of perspiration, such as astringents based on aluminium salts, and in particular based on aluminium hydroxychloride, are known. The formation of bad odours can be suppressed with these agents in that their immediate cause, that is to say the development of perspiration through the epidermis, is suppressed (cf. DE-A 21 37 926). In contrast to these antiperspirants, cosmetic compositions having a deodorizing action are a class of compositions which, although they have no action or only a slight action on the volume of perspiration, on the basis of their bactericidal action destroy the bacteria which lead to decomposition of the perspiration. These include compositions having a content of antimicrobial substances. Among the compounds having such properties, for example, phenol derivatives with and without halogen substituents, organic mercury compounds, quaternary ammonium compounds, such as Cequartyl® or certain ion exchangers or metal chelates of 1,3-diketones, as well as derivatives of amino acids having a disinfecting action have become known.

Phenyl hydroxyalkyl ethers, in particular the compound known by the name phenoxyethanol, have furthermore been employed as preservatives on the basis of their bactericidal and fungicidal actions on a number of microorganisms. Phenoxyethanol is active and completely non-toxic, above all in an acid and neutral medium, but also in an alkaline medium. It provides adequate protection even at low concentrations. Because of its neutral smell, it rapidly found acceptance in the pharmaceuticals and cosmetics industry. However, its action is chiefly directed against Gram-negative bacteria.

From the chemical aspect, phenoxyethanol is largely inert when used. It is a colourless, slightly viscous liquid with a weak, pleasant smell and an astringent taste, and is miscible with acetone, ethyl alcohol and glycerol and soluble in water (1:45) and fats, for example olive oil and ground nut oil (1:50).

However, the solubility of phenoxyethanol in water is low and is not adequate for some preservation purposes.

Phenoxyethanol, which is adequately described in the literature, has been detected in nature in tropical fruits, in Cichorium endivia and in green tea (Camellia sinensis). It has a mild, rose-like fragrance and is also employed as a fixative for perfume compositions.

It is also known from GB-B 11 55 789 to employ certain phenyl ethers as antibacterial agents in cleansing compositions for the skin. Substituted phenyl ethers are moreover used as antibacterial agents (cf. DE Offenlegungsschrift 16 42 057).

In a further development of the principle described above, attempts have therefore been made additionally to use the antimicrobial properties of certain odoriferous substances, essential oils or other perfume constituents and to employ these as antimicrobial and deodorizing active compounds in deodorizing perfume compositions. DE-A 27 28 921 and DE-A 33 15 058 describe the natural substance farnesol (for example 2-trans,6-trans-3,7,11-trimethyldodeca-2,6,10-trien-1-ol) and its 3 synthetic isomers as such an antimicrobially active substance which severely inhibits the growth of odour-forming bacteria on the skin without greatly changing the overall bacterial flora of the skin. A disadvantage here is, however, that when used as a deodorizing, antimicrobial active compound, these compounds must be employed in considerably higher concentrations than in customary perfume compositions in order to achieve the desired deodorizing action.

Thus, for example, a concentration of at least 0.3% by weight of farnesol, based on the cosmetic composition, is required for complete inhibition of growth of the Gram-positive bacteria Staphylococcus aureus and Staphylococcus epidermidis and for substantial inhibition is of Corynebacterium spec. In odoriferous substance compositions and in products having a deodorizing action, the content of farnesol is 0.2 to 0.5%.

Farnesol (3,7,11-trimethyldodeca-2,6,10-trien-1-ol) is an acyclic primary sesquiterpene alcohol, the natural occurrence of which has been adequately documented in the literature. Thus, it is found in lemongrass oil, palmarosa oil, citronella oil, tuberose flower oil, sandalwood oil, linden blossom oil and in many other natural substances.

It is a colourless liquid with a typical smell and soluble in 3 parts of ethyl alcohol (70%) to give a clear solution.

Glycerol monoesters of short-chain and medium-chain fatty acids are also already known as an auxiliary for preservation in cosmetic compositions.

Glycerol monolaurate, known under the trade name Lauricidin® (Dragoco), is also to be regarded as a germicide which is suitable for cosmetic compositions. It is dispersible in water, soluble in alcohol, fats and paraffin oil and miscible with acetone.

Such glycerol monoesters and glycerol monolaurate are detected in nature at least as metabolism products during digestion of edible fats. Various monoglycerides are therefore customary as additives in the foodstuffs industry. Glycerol monolaurate and glycerol monocaprylate are used as a pharmaceutical ointment base, as co-emulsifiers for emulsions and as components which impart consistency to the most diverse cosmetic compositions, such as shampoo, bath additives, creams or lotions.

However, these two classes of compositions mentioned above are not completely satisfactory, because, on the one hand, the astringent compositions or antiperspirant compositions suppress the natural phenomenon of formation of perspiration and moreover have an adverse action on the epidermis, and, on the other hand, some of the bactericidal compositions have the disadvantage that they completely destroy the microbe flora of the skin and consequently substantially interfere with the biological equilibrium of the epidermis.

Furthermore, the majority of these compositions have a slightly phenolic smell. For this reason, efforts to prepare cosmetic compositions which have a very good deodorizing action and a neutral smell and are free from side effects continue to be appropriate.

Deodorants which dispense with the traditional active compounds mentioned have indeed become known recently. For example, attempts have been made to solve the deo problem exclusively via perfume. The body odour components are said to be neutralized to a certain extent as a fragrance complex of the perfume such that the adverse body odour is covered up for some time.

However, the action of these deodorizing cosmetic compositions is inadequate for the requirements in practice as regards action potency (masking of odour) and duration of action.

The antibacterial properties of certain odoriferous substances, essential oils or other perfume constituents, individually or as a mixture, are furthermore used in that deodorizing perfume compositions are made up as such. Such products have a deodorizing action over a relatively long period of time both via the fragrance and via the antibacterial action.

Finally, a group of substances which prevent, by means of enzyme inhibition, unpleasantly smelling decomposition products forming from the contents of perspiration, residues of the horny layer and skin surface oil may also be mentioned.

However, even if the risk of skin irritation when deodorants are used is not caused to the same extent as when antiperspirants are used, intolerances, photosensitizations and toxic side effects of different intensity occasionally occur when deodorants are used constantly.

A frequent disadvantage of such deodorizing active compounds is that not only are the bacteria responsible for the body odour prevented from growing or killed, but furthermore other bacteria of the bacterial skin flora are also destroyed. Such deodorizing active compounds thus have a considerably more potent action in an undesirable manner than would be necessary for avoiding body odour.

A combination of the active compounds described above, i.e. phenoxyethanol, farnesol and glycerol monolaurate, which has a deodorizing action is already known from European Patent Application EP-A-297 310. However, it has not always proved to be so completely satisfactory in all aspects that no improvements would be conceivable.

A completely satisfactory deo-composition is linked with the following prerequisites:

1) Preservation of the natural biology of the skin
2) Fragrance neutrality
3) High activity only in respect of deodorizing, i.e. only avoidance and/or elimination of body odour
4) Avoidance of the formation of resistant bacterial strains
5) Harmlessness in the event of an overdose or if used otherwise not as intended
6) Good cosmetic use and performance
7) Easy handling (for example as a liquid) and universal usability in the most diverse cosmetic and external formulations
8) Excellent skin and mucosa tolerance
9) Use of environment-friendly substances
10) Recourse to natural systems or substances which occur in nature having status (GRAS, RFM and the like)
11) Buffer capacity The object of the invention was therefore to provide a new, highly active deodorizing or antimicrobial composition based on starting substances which occur in nature or are close to nature such as, for example, essential oils or fragrances, which, while protecting the natural biology of the skin as far as possible, has an effective deodorizing action, can be employed universally in the most diverse deodorizing cosmetic compositions and, for example, can require smaller amounts to be employed here than the prior art known to date envisages.

It has been found, and therein lies the achievement of this object, that a composition of one or more 3,7,11-trimethyl-2,6,10-dodecatrien-1-ols, a phenyl hydroxyalkyl ether having one, two or three C atoms in the alkyl radical and at least one glycerol monoester of a short-chain or medium-chain fatty acid meets the abovementioned requirements, it being possible for this composition optionally also to comprise glycerol monolaurate as well.

The invention therefore relates to deodorizing or antimicrobial compositions, in particular for use in cosmetic or topical formulations, characterized in that they comprise a) at least one 3,7,11-trimethyl-2,6,10-dodecatrien-1-ol,
b) at least one phenyl hydroxyalkyl ether having one, two or three carbon atoms in the alkyl radical,
c) at least one glycerol monoester of a short-chain or medium-chain fatty acid and
d) optionally glycerol monolaurate.

The compositions according to the invention with components a), b) and c) comprise, for example, in each case based on the total weight of the compositions, a) 10–50, preferably 15–40% by weight of one or more 3,7,11-trimethyl-2,6,10-dodecatrien-1-ols,
b) 5–45, preferably 10–35% by weight of at least one phenyl hydroxyalkyl ether having a maximum of 3 C atoms in the alkyl radical and
c) 10–80, preferably 25–75% by weight of at least one glycerol monoester of a short-chain or medium-chain fatty acid, the amounts being chosen such that the sum of a), b) and c) gives 100% by weight.

In compositions which, in addition to the three components a), b) and c) according to the invention, also additionally comprise the fourth component d) according to the invention, glycerol monolaurate, the weight contents of components a), b) and c) are varied, the amounts by weight being chosen such that the sum of a), b), c) and d) gives 100% by weight.

The proportion by weight of glycerol monolaurate is preferably 1 to 20% by weight, in particular 5 to 15% by weight, in each case based on the total weight of the four components.

Compositions according to the invention with components a), b), c) and d) comprise, for example, in each case based on the total weight of the compositions, a) 10–45, preferably 15–35% by weight of one or more 3,7,11-trimethyl-2,6,10-dodecatrien-1-ols,
b) 5–40, preferably 10–30% by weight, of at least one phenyl hydroxyalkyl ether having a maximum of 3 C atoms in the alkyl radical,
c) 10–70, preferably 25–65% by weight of at least one glycerol monoester of a short-chain or medium-chain fatty acid and
d) 1–20, preferably 5–15% by weight of glycerol monolaurate, the amounts being chosen such that the sum of a), b), c) and d) gives 100% by weight.

The various 3,7,11-trimethyl-2,6,10-dodecatrien-1-ols, preferably the natural substance farnesol and its geometric isomers, can be employed here individually or in the form of any desired mixture.

The phenyl hydroxyalkyl ethers having 1 to 3 C atoms in the alkyl radical employed in the compositions according to the invention are preferably those in which the hydroxyl group on the alkyl radical is in the terminal position. An ether or a mixture of several ethers can be used. The use of phenoxyethanols (ethylene glycol monophenyl ethers), for example 2-phenoxyethanol, is particularly preferred. It is used in the deodorizing antimicrobial composition according to the invention, for example in amounts of 5 to 45% by weight, preferably 10 to 35% by weight, preferably individually, but also as a mixture with these other ethers.

Suitable glycerol monoesters of a short-chain or medium-chain fatty acid preferably contain fatty acids having 3–11 carbon atoms, particularly preferably 6–10 carbon atoms, in particular 6–8 carbon atoms. The fatty acids are preferably saturated. The alkyls can be straight-chain or branched, and straight-chain alkyl is preferred. Preferably, a terminal OH group of the glycerol is esterified. One glycerol monoester or a mixture of several esters can be used.

Glycerol monocaprylate is particularly preferred. It is obtainable under the trade name Monocaprylin (Straetmanns). It is preferably esterified on the terminal OH group.

Glycerol monolaurate is known and is obtainable under the trade name Lauricidin (Dragoco). The terminal OR group is preferably esterified.

Although certain antimicrobial properties were also already known for ethylene glycol monophenyl ether (U.S. Pat. No. 2,451,149) and glycerol monolaurate, the compositions according to the invention proved to be significantly more active in a surprising and unforeseeable manner than was to be expected for the sum of the individual components.

In microbiological studies, a synergistic action of the compositions according to the invention was detected for germs relevant to the deodorizing action in the form such that an active amount of the compositions according to the invention had a significantly more potent microbicidal action than could be expected from the sum of the activities of the individual components. The synergistic action was confirmed with the aid of microbiological activity tests.

When used in topical or cosmetic formulations, the deodorizing and antimicrobial compositions according to the invention, compared with the individual components, therefore also have an adequate action, for example if smaller amounts are employed, or, in the same amounts, have a more potent action or act for a longer time.

Deodorant compositions obtained with the compositions according to the invention can be used for treatment of the armpits, the feet, the body surface and the hair or the genital region. They are used in a known manner by a single or several applications daily.

Another advantage of the compositions according to the invention is that they can be employed without problems in the various types of recipes for deodorizing cosmetic compositions, such as, for example, roll-on, stick, powder, lotion, spray or powder spray, deo soap or solution.

Direct incorporation of the synergistic compositions according to the invention into external formulations and topical and cosmetic compositions has the advantage that homogeneous distribution of the components is ensured and time-consuming addition of the individual components is thus eliminated.

Deodorizing cosmetic compositions which comprise, in addition to customary constituents, an active amount of the compositions according to the invention as the deodorizing active compound therefore represent a preferred embodiment of the invention. Deodorizing cosmetic compositions which have, for example, a content of 0.01 to 10% by weight, preferably a content of 0.05 to 5.00% by weight, in particular 0.1 to 0.9% by weight, based on the total amount of the cosmetic composition, of the deodorizing and antimicrobial compositions according to the invention have proved to be particularly advantageous in this embodiment of the invention.

Chemiluminescence measurements on the skin reveal here that the good deodorizing action of the compositions according to the invention is also to be attributed to oxidative reactions which are induced by the composition according to the invention, in addition to the antimicrobial action.

All the objects described are achieved with the compositions and agents according to the invention.

The cosmetic deodorants according to the invention with the compositions according to the invention can be in the form of aerosols, that is to say preparations which can be sprayed from aerosol containers, squeeze bottles or by a pump device, or in the form of liquid compositions which can be applied by means of roll-on devices, as deo sticks and in the form of W/O or O/W emulsions, for example creams or lotions, which can be applied from normal bottles and containers. The cosmetic deodorants can furthermore advantageously be in the form of deodorizing tinctures, deodorizing intimate cleansing compositions, deodorizing shampoos, deodorizing shower or bath formulations, deodorizing powders or deodorizing powder sprays.

In addition to water, ethanol and isopropanol, glycerol and propylene glycol, customary cosmetic carriers which can be employed for preparation of the deodorizing formulations according to the invention are skincare fats or fatlike substances, such as decyl oleate, cetyl alcohol, cetyl stearyl alcohol and 2-octyldodecanol, in the ratios of amounts customary for such preparations, as well as muciferous substances and thickeners, for example hydroxyethyl- or hydroxypropyl-cellulose, polyacrylic acid and polyvinylpyrrolidone, and also, in small amounts, cyclic silicone oils (polydimethylsiloxanes) as well as liquid polymethylphenylsiloxanes of low viscosity.

Suitable propellants for cosmetic deodorants according to the invention which can be sprayed from aerosol containers are the customary known readily volatile liquefied propellants, for example hydrocarbons (propane, butane or isobutane), which can be employed by themselves or as a mixture with one another. Compressed air can also advantageously be used.

The expert of course knows that there are propellant gases which are non-toxic per se and would be suitable in principle for the present invention, but which should nevertheless be omitted because of an unacceptable action on the environment or other concomitant circumstances, in particular chlorofluorocarbons (CFCs).

Emulsifiers which have proved suitable for preparation of the cosmetic deodorants according to the invention which are advantageously to be applied to the desired areas of skin as liquid formulations by means of a roll-on device, it being possible for these emulsifiers to be used in the formulations in a small amount, for example 2 to 5% by weight, based on the total composition, are nonionic types, such as polyoxyethylene fatty alcohol ethers, for example cetostearyl alcohol polyethylene glycol ether having 12 or 20 ethylene oxide units added on per molecule, cetostearyl alcohol and sorbitan esters and sorbitan ester-ethylene oxide compounds (for example sorbitan monostearate and polyoxyethylene sorbitan monostearate), and long-chain higher molecular weight waxlike polyglycol ethers.

In addition to the constituents mentioned, fragrance, colorants, antioxidants (for example α-tocopherol and its derivatives or butylated hydroxytoluene (BHT=2,6-di-tert-butyl-4-methylphenol) in amounts of 0.01 to 0.03%, based on the total composition), suspending agents, buffer mixtures or other customary cosmetic base substances can be admixed to the deodorizing cosmetic formulations according to the invention, the pH of which is preferably brought to 4.0 to 9.0, in particular 5.0 to 6.5, for example, by customary buffer mixtures.

The pH of the formulations according to the invention is advantageously brought to the weakly acid to weakly alkaline range, preferably 4.0–9.0, particularly preferably 5.0–6.5.

The particular amounts of cosmetic carriers and fragrance to be employed can easily be determined by the expert by simple trial and error according to the nature of the particular product.

Those substances and perfume oils which are stable, do not irritate the skin and already have antibacterial or bacteriostatic properties as such are also suitable, if appropriate, for perfuming.

Apart from special formulations which are noted separately in each case in the examples, the cosmetic formulations are prepared in the customary manner, usually by simple mixing with stirring, if appropriate with gentle heating. The preparation presents no difficulties. For emulsions, the oily phase and the aqueous phase are prepared separately, for example, if appropriate with heating, and are then emulsified.

The customary rules for compiling cosmetic formulations, with which the expert is familiar, are otherwise to be observed.

If the esters according to the invention are to be incorporated into powder sprays, the suspension bases for this can advantageously be chosen from the group consisting of silicic acid gels (for example those which are obtainable under the trade name Aerosil®), kieselguhr, talc, modified starch, titanium dioxide, silk powder, nylon powder, polyethylene powder and related substances.

Another advantageous embodiment of the invention is the use of the deodorizing and antimicrobial compositions according to the invention as antimicrobial active compounds for stabilizing topical or cosmetic formulations against decomposition by microorganisms.

The abovementioned amounts can be used. Amounts of 0.3–0.75% by weight, based on the total weight, are particularly preferred.

In the context of the present application, unless stated otherwise, amounts and percentage data are based on the weight and the total composition of the particular formulations.

The following examples are intended to illustrate the invention, but without the intention being to limit the invention to these examples.

EXAMPLE 1

The following mixtures A–F were brought together in a dissolving tank with a stirring device and were stirred at room temperature until a homogeneous solution had formed:

| Component | Composition: | | | | | |
|---|---|---|---|---|---|---|
| | A | B | C | D | E | F |
| I | 34 | 34 | 10 | 30 | 25 | 8 |
| II | 13 | 25 | 75 | 13 | 25 | 75 |
| III | 0 | 0 | 0 | 10 | 7 | 7 |
| IV | 53 | 41 | 15 | 47 | 43 | 10 |

Component
I: 3,7,11-trimethyl-2,6,10-dodecatrien-1-ol (isomer mixture of 4 isomers, farnesol No. 2/027040 from Dragoco, Holzminden)
II: glycerol 1-monocaprylate (Monocaprylin)
III: glycerol 1-monolaurate (Lauricidin)
IV: 2-phenoxyethanol The antimicrobial activity of the abovementioned compositions according to the invention was investigated with the aid of dying kinetics in comparison with the individual components. The substances were employed in dilution series as solutions or dispersions in water.

The deodorizing cosmetic compositions listed in Examples 2 to 10 were prepared by the processes which are customary for the particular compositions and are known to the expert. The abbreviation PW here means parts by weight and the abbreviation EO represents ethylene oxide units.

The composition A, B, C, D, E or F according to the invention employed in the following examples is always in each case one of these compositions (A–F) mentioned in Example 1, in the stated amount by weight, so that all the compositions are used (individually) in succession.

EXAMPLE 2

| Roll-on deodorant: | |
|---|---|
| Methylcellulose (Viskontran® HEC 30 000) | 0.80 PW |
| Water | 52.00 PW |
| Ethoxylated glycerol monococoate 7EO (Cetiol® HE) | 1.00 PW |
| Hydrogenated castor oil 40 EO (Cremophor® RH40) | 2.50 PW |
| Ethanol | 39.20 PW |
| 1,2-propylene glycol | 3.00 PW |
| Fragrance | 1.00 PW |
| Composition A, B, C, D, E or F, according to the invention, from Example 1 | 0.15 PW |
| 0.025% strength colour solution | 0.35 PW |

EXAMPLE 3

| Deodorizing stick: | |
|---|---|
| 1,2-propylene glycol | 46.00 PW |
| Stearic acid | 7.00 PW |
| Ethyl alcohol | 35.10 PW |
| Water | 10.00 PW |
| NaOH lozenges | 1.20 PW |
| Fragrance | 0.50 PW |
| Composition A, B, C, D, E or F, according to the invention, from Example 1 | 0.20 PW |

EXAMPLE 4

| Deodorizing lotion (viscous): | |
|---|---|
| Polyethylene glycol 20 oleyl ether (Cremophor®0) | 2.00 PW |
| Cetylstearyl alcohol | 3.00 PW |
| Paraffin oil | 5.00 PW |
| 1,2-propylene glycol | 3.00 PW |
| Polyvinylpyrrolidone (Luviskol®K30) | 0.50 PW |
| Composition A, B, C, D, E or F, according to the invention, from Example 1 | 0.15 PW |
| Water | 89.90 PW |
| Perfume | 0.45 PW |

EXAMPLE 5

| Deodorizing lotion (thinly liquid): | |
| --- | --- |
| Ethoxylated fatty alcohol 6 EO (Cremophor<sup>R</sup>A) | 1.00 PW |
| Polyethylene glycol 20-oleyl ether (Cremophor<sup>R</sup>O) | 1.00 PW |
| Glycerol monostearate | 2.00 PW |
| Cetyl alcohol | 1.00 PW |
| Isopropyl myristate | 2.00 PW |
| Glycerol | 1.00 PW |
| Polyvinylpyrrolidone (Luviskol<sup>R</sup>K30) | 0.50 PW |
| Composition A, B, C, D, E or F, according to the invention, from Example 1 | 0.15 PW |
| Water | 90.90 PW |
| Fragrance | 0.45 PW |

EXAMPLE 6

| Deodorizing pump spray (not aerosol) | |
| --- | --- |
| Ethanol | 61.50 PW |
| Ethoxylated glycerol monococoate 7EO (Cetiol<sup>R</sup>HE) | 1.50 PW |
| Composition A, B, C, D, E or F, according to the invention, from Example 1 | 0.40 PW |
| Citric acid | 0.02 PW |
| Water | 36.18 PW |

EXAMPLE 7

| Deodorizing body spray (aerosol) | |
| --- | --- |
| Ethanol | 21.35 PW |
| 1,2-propylene glycol | 3.00 PW |
| Octyldodecanol (Eutanol<sup>R</sup>G) | 0.04 PW |
| Fragrance | 0.50 PW |
| Composition A, B, C, D, E or F, according the invention, from Example 1 | 0.10 PW |
| Isopropyl myristate | 0.01 PW |
| Propellant gas | 75.00 PW |

EXAMPLE 8

| Deodorizing intimate washing solution | |
| --- | --- |
| 30% strength cocoamidopropyl betaine (Tego-Betain<sup>R</sup>L7) | 10.00 PW |
| Ethoxylated glycerol monolaurate 22EO (Tagat<sup>R</sup>L2) | 2.00 PW |
| Composition A, B, C, D, E or F, according to the invention, from Example 1 | 0.10 PW |
| 80% strength lactic acid | 0.50 PW |
| Fragrance | 0.08 PW |
| Water | 87.32 PW |

EXAMPLE 9

| Deodorizing composition (liquid) to counter hair odour | |
| --- | --- |
| Polyethylene glycol 400 | 0.20 PW |
| Ethanol | 37.50 PW |
| Fragrance | 0.10 PW |
| Composition A, B, C, D, E or F, according to the invention, from Example 1 | 0.10 PW |
| Hydrogenated castor oil 40 EO (Cremophor<sup>R</sup>RH 40) | 0.20 PW |
| Citric acid | 0.01 PW |
| Water | 61.89 PW |

EXAMPLE 10

| Deodorizing soap | |
| --- | --- |
| Base soap 80/20 (approximately 78% fatty acid) | 96.84 PW |
| Superfatting agent | 1.45 PW |
| Colorants | 0.01 PW |
| Antioxidant | 0.05 PW |
| Fragrance | 1.07 PW |
| Titanium dioxide | 0.19 PW |
| Composition A, B, C, D, E or F, according to the invention, from Example 1 | 0.39 PW |
| | 100.00 PW |

We claim:

1. Deodorizing or antibacterial compositions, in particular for use in cosmetic or topical formulations, comprising
   a) at least one 3,7,11-trimethyl-2,6,10-dodecatrien-1-ol,
   b) at least one phenyl hydroxyalkyl ether having one, two or three carbon atoms in the alkyl radical,
   c) at least one glycerol monoester of a $C_3$–$C_{11}$-fatty acid and
   d) optionally glycerol monolaurate.

2. Compositions according to claim 1, comprising 1–20% by weight of glycerol monolaurate.

3. Compositions with components a), b) and c) according to claim 1, which comprise, in each case based on the total weight of the compositions,
   a) 10–50% by weight of one or more 3,7,11-trimethyl-2,6,10-dodecatrien-ols,
   b) 5–45% by weight of at least one phenyl hydroxyalkyl ether having a maximum of 3 C atoms in the alkyl radical and
   c) 10–80% by weight of at least one glycerol monoester of a $C_3$–$C_{11}$-fatty acid.

4. Compositions with components a), b), c) and d) according to claim 1, which comprise, in each case based on the total weight of the compositions,
   a) 10–45% by weight of one or more 3,7,11-trimethyl-2,6,10-dodecatrien-1-ols,
   b) 5–40% by weight, of at least one phenyl hydroxyalkyl ether having a maximum of 3 C atoms in the alkyl radical,
   c) 10–70% by weight of at least one glycerol monoester of a $C_3$–$C_{11}$-fatty acid and
   d) 1–20% by weight of glycerol monolaurate.

5. Deodorizing cosmetic compositions comprising, in addition to customary constituents, an active amount of the compositions according to claim 1 as the deodorizing active compound.

6. Deodorizing cosmetic compositions comprising 0.01 to 10% by weight, based on the total amount of the cosmetic composition, of the compositions according to claim 1.

7. Compositions according to claim 1, wherein said phenyl hydroxyalkyl ether having a maximum of 3 C atoms in the alkyl radical is 2-phenoxyethanol.

8. Compositions according to claim 1, wherein said glycerol monoester is glycerol monocaprylate.

9. A method for stabilizing topical or cosmetic formulations which comprises adding to such formulations a composition according to claim 1.

10. The method of claim 9, wherein said composition is added in an amount of from 0.1 to 10% by weight, based on the total weight of formulation.

* * * * *